(12) United States Patent
Seyr et al.

(10) Patent No.: US 6,736,847 B2
(45) Date of Patent: May 18, 2004

(54) ANCHORING DEVICE

(75) Inventors: Volkmar Seyr, Ampass (AT); Helmut Goreis, Innsbruck (AT); Clive Reay-Young, Harrogate (GB)

(73) Assignee: Arthrocare Corporation, Sunnyvale, CA (US)

( * ) Notice: Subject to any disclaimer, the term of this patent is extended or adjusted under 35 U.S.C. 154(b) by 0 days.

(21) Appl. No.: 10/187,418

(22) Filed: Jul. 2, 2002

(65) Prior Publication Data

US 2003/0009220 A1 Jan. 9, 2003

(30) Foreign Application Priority Data

Jul. 7, 2001 (GB) .............................................. 0116605

(51) Int. Cl.[7] .............................. A61F 2/08; A61B 17/56
(52) U.S. Cl. ........................ 623/13.14; 606/72; 411/28; 411/79
(58) Field of Search ........................ 623/13.14; 606/232, 606/72; 411/27, 28, 25, 24, 456, 32, 33, 75, 76, 77, 78, 79

(56) References Cited

U.S. PATENT DOCUMENTS

| | | | | |
|---|---|---|---|---|
| 3,974,621 A | * | 8/1976 | Stang | ........................... 411/75 |
| 5,037,422 A | | 8/1991 | Hayhurst et al. | |
| 5,324,308 A | | 6/1994 | Pierce | |
| 5,405,359 A | | 4/1995 | Pierce | |
| 5,529,424 A | * | 6/1996 | Neubert et al. | ............. 403/298 |
| 5,632,748 A | | 5/1997 | Beck, Jr. et al. | |
| 5,645,588 A | | 7/1997 | Graf et al. | |
| 5,984,966 A | * | 11/1999 | Kiema et al. | ............ 623/13.14 |
| 6,379,361 B1 | * | 4/2002 | Beck et al. | ................... 606/72 |

FOREIGN PATENT DOCUMENTS

| | | |
|---|---|---|
| EP | 0 619 982 A2 | 10/1994 |
| EP | 1 066 805 A2 | 1/2001 |
| WO | 98/22048 A1 | 5/1998 |

* cited by examiner

*Primary Examiner*—David H. Willse
*Assistant Examiner*—Thomas J Sweet
(74) *Attorney, Agent, or Firm*—John T. Raffle; Richard R. Batt

(57) ABSTRACT

The invention relates to an anchoring device for urging a ligament transplant against the wall of a bone hole during ligament replacement and for fixing the anchor in position in the said bone hole. The device has a first component and a second component designed for mutual sliding co-operation between a first anchor inserting position and a second fixation position. The sliding co-operation is provided along respective parallel inner mating surfaces of each component which surfaces are each in angular relation to the respective component outer surfaces and in opposed angular relation to each other so that in the anchor insertion position the width of the said anchoring device is in an elongate narrow mode with respect to a bone hole and, in the fixation position, the width of the said anchoring device is in a compressed wide mode to thereby urge the ligament against the wall of the bone hole. A method of ligament fixation in a bone hole is also disclosed.

28 Claims, 4 Drawing Sheets

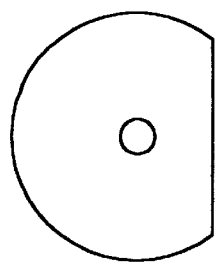
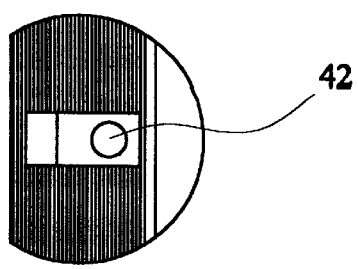
FIG. 3(b)
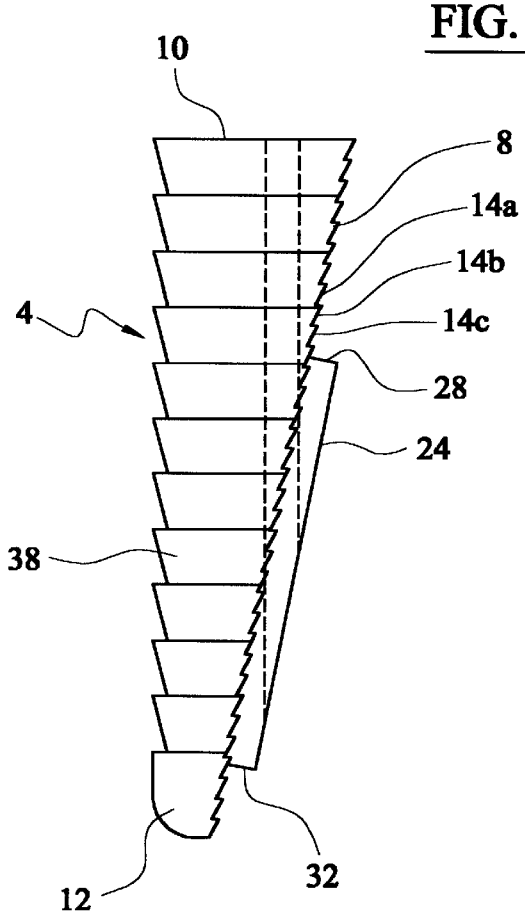
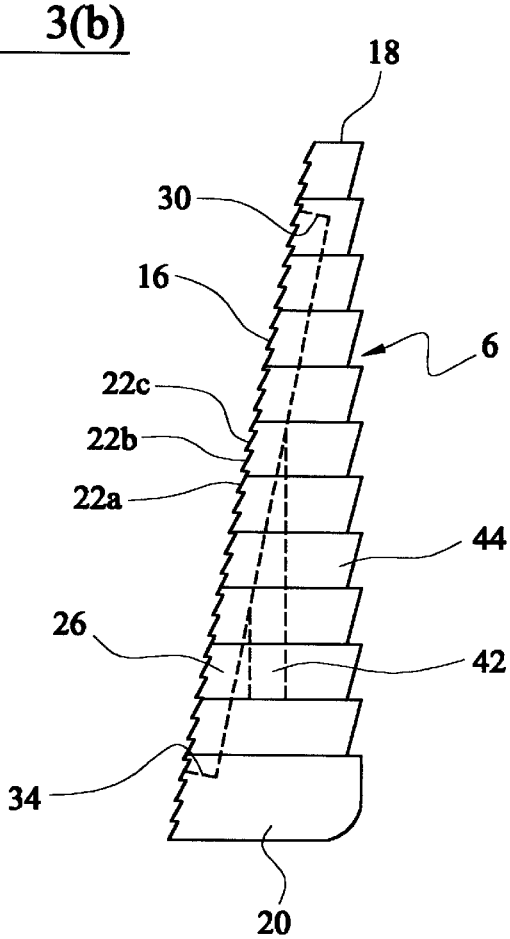
FIG. 1          FIG. 2
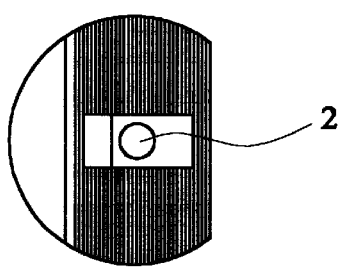
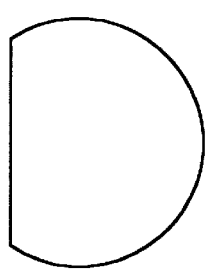
FIG. 3(a)

ANCHORING DEVICE

United Kingdom Patent Application No. 0116605.7 filed in Jul. 7, 2001 is incorporated herein by reference.

The present invention relates to an anchoring device and, in particular, but not exclusively, to an anchoring device for urging a ligament transplant against the wall of a bone hole during ligament replacement and for fixing the anchor in position in the said bone hole.

Due to increasing involvement of people with active sport, injuries are becoming increasingly common where tissues such as ligaments or tendons tear or detach from bone. Surgical techniques have been developed to reconstruct such torn soft tissues and to re-attach them to the relevant bone. One of the most common types of such injuries is tearing of the Anterior Cruciate Ligament (ACL). The Anterior Cruciate Ligament connects the femur to the tibia at the centre of the knee joint. Reconstruction of such tissues generally involves replacement with a graft such as autologous or artificial tendon. An autologous tendon graft may be taken from the patients patellar tendon or, alternatively, the semitendinosus may be utilised. A typical fixation technique involves the use of a circular button fixation device which is located on the outside of the femur above the knee. As this is some distance from the site where the graft will be utilised in the knee joint, sutures are used to attach the graft to a femur button. The main disadvantage of this technique is that incisions need to be made through the skin and quadriceps muscle resulting in trauma to the leg and a cosmetically undesirable procedure.

Use of the femur button also involves laborious measurement of lengths and drilling with two drill diameters.

U.S. Pat. No. 5,645,588 describes an improved technique whereby the ligament anchor may be threaded through a femoral tunnel formed through the femur from the centre of the knee.

PCT/US97/22061 provides an interference fit insertion element with a proximal aperture through which a graft may be threaded or attached. The technique involves securement of the interference end of the device into the central cancellous area of the bone.

U.S. Pat. No. 5,037,422 also relates to the anchoring of sutures for securement of a suture to a bore hole in a bone. The device is shown secured to the cancellous bone. The device is for use in soft tissue fixation to the outside of the bone and not fixation within the bone hole itself.

A device for graft fixation using sutures is described in EP 0 619 982 where the anchor includes a body and a plurality of barbs located in axially aligned, circumferentially spaced relation to each other about the body. The barbs have a normal configuration wherein they extend rearwardly and radially outwardly from the anchor body to outer ends which are normally located outside a longitudinal projection of the largest geometric cross-section of the body transverse to its longitudinal axis. The device relies upon interference between the barbs and the soft cancellous bone area. This interference fit is not only difficult to insert for reasons of space but also involves some risk of damage to the transplant.

Interference fit bone anchors are, therefore, increasingly common for ligament fixation. A problem for the surgeon fitting the device is how to insert the device without the interfering projections impeding the initial location in the closely fitting bone hole. EP 1066805 solves this problem by using a cruciform device which expands at the distal end when the replacement ligament is tensioned ie. after the cruciform anchor has been located in position.

Nevertheless, there is still a general problem in the prior art in how to easily insert an anchor which is designed to be a very tight fit in a bone hole.

According to a first aspect of the present invention there is provided an anchoring device for urging a ligament against a bone surface within a tunnel formed in a bone of a patient comprising a first component and a second component, the first and second component being designed for mutual sliding co-operation between a first anchor inserting position and a second fixation position, said sliding co-operation being provided along respective parallel inner mating surfaces of each component which surfaces are each in angular relation to the respective component outer surfaces and in opposed angular relation to each other so that in the anchor insertion position the width of the said anchoring device is in an elongate narrow mode with respect to a bone hole and, in the fixation position, the width of the said anchoring device is in a compressed wide mode to thereby urge the ligament against the wall of the bone hole.

Preferably, the first and second component include mutual engaging means on their respective inner surfaces for multiple position fixation.

Preferably, the first or second component has an elongate tongue and the second or first component respectively has an accommodating elongate groove wherein the tongue slides in the groove between the said anchor inserting and fixating positions.

The first and second component each have a leading end which is inserted into the bone hole first and a trailing end which is opposite the leading end.

Preferably, the anchor device includes a terminal abutment at the trailing end ie. remote from the inner end of the bone hole to thereby provide a limit of extension of the anchor.

Preferably, the anchor also includes a terminal abutment at the leading end ie. the end adjacent to the inner end of the bone hole, in use, to provide a limit of longitudinal compression of the trailing component of the anchor. Preferably, the leading ends of the first and second components and the location of the leading end terminal abutment are such that the respective leading ends are substantially contiguous at the limit of compression to prevent damage to ligament located thereover. Advantageously, the terminal abutment improves the lateral interlocking of the anchor device, preferably provided by a tongue and groove arrangement, by extending it to terminal interlocking at the limits of elongation and compression.

Preferably, the trailing ends are also substantially contiguous at the limit of said compression. Preferably, therefore, the respective leading ends and respective trailing ends are axially displaced from each other in the elongate inserting position of the anchor device.

Further grooves may be provided on the outer surface of the first and/or second component to conveniently locate and guide a ligament transplant thereon. The grooves are positioned so that the transplant may loop over the leading ends of the anchor device or they may be designed to accommodate the transplant on one side of the device.

Preferably, an elongate positioning bore is provided in the anchor device. Preferably, the said bore extends in two sections through both the first and second component in such a manner that the bore sections are aligned in the said first elongate position. Advantageously, a positioning tool can be inserted through both bore sections in the said first position to thereby lock the two mating inner surfaces and hence the two components together during insertion in the bone hole.

An insertion takes place with the components in the elongate position, the leading component is located in the fixation position whilst the other component remains in the trailing position.

After insertion is complete, the positioning member is removed so that the trailing component may be pushed into the fixation position. Pushing the trailing component into position progressively widens the anchor device to thereby urge the transplant against the walls of the bone hole and secure the anchor in position.

The mutual engaging means provide incremental means to increasingly widen the anchor in the bone hole until a secure width is obtained, preferably, the secure width is that width wherein the leading ends of the first and second component become contiguous.

In one embodiment, the first component is shaped in the form of a blade, the outer edge of the said blade (ie. the edge adjacent the walls of the bone hole in use) projecting out from the second component and the inner edge, preferably, providing the tongue for sliding in the groove of the second component. In this manner, the portion of the sides of the blade which project from the surface of the second component and a portion of the surface of the second component adjacent to the said projecting surface may provide an elongate recess for location of the transplant on either side thereof.

The leading and/or trailing ends of the blade may be suitably stepped with respect to the respective leading and trailing ends of the tongue section to co-operate with respective terminal abutments in the groove and still provide contiguity with the second component in the fixation position.

In any embodiment, the mutual engaging means may be provided between mating surfaces, preferably along inner surfaces adjacent to the tongue and/or groove and extending outwards substantially perpendicular thereto.

According to a second aspect of the present invention there is provided a method of ligament fixation in a bone hole comprising the steps of:

forming a tunnel in a bone;
inserting a ligament transplant and an anchor device according to the first aspect of the invention in the bone hole whilst in the anchor insertion or elongate position of the said device; and
urging the trailing component into the fixating position to thereby urge the transplant against the bone hole and to fix the anchor in the said bone hole.
Preferably, the method includes the steps of:
inserting a positioning tool into the anchor device in the said first position prior to locating the anchor device in the bone hole and utilising the positioning tool to locate the anchor device in the bone hole.

Preferably, the positioning tool is removed prior to urging the anchor device into the fixating position.

The outer surfaces of the anchor device may include projections to aid fixation in the bone hole. Various types of projections are present in the art and will be known to those skilled in the art.

The inner or leading end of the anchor device may be planar or semispherical or any other of the suitable shapes which are known to those skilled in the art.

Although the anchor device is expected to be used in ligament fixation, it can be used in other fixation operations where securement of an anchor device in a bone hole is necessary, for instance, bone plate fixation onto the surface of a bone.

The invention will now be described, by way of example only, with reference to the accompanying drawings in which:

FIG. 1 shows a side elevation of a component of an anchoring device in accordance with the present invention;

FIG. 2 shows a side elevation of a component of an anchoring device in accordance with the present invention;

FIG. 3a shows the leading end of the anchoring device of FIG. 1 in accordance with the present invention;

FIG. 3b shows the trailing end of the anchoring device of FIG. 2 in accordance with the present invention;

Figure 4:
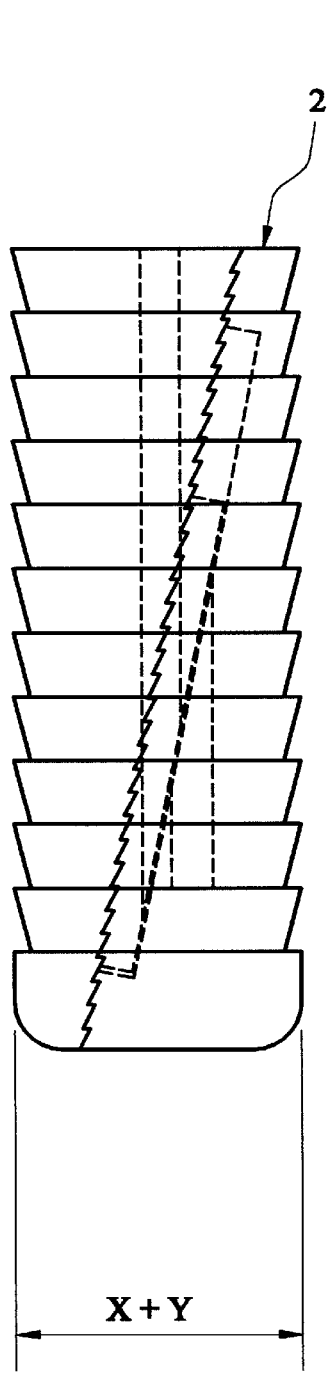
FIG. 4 shows a side elevation of the anchoring device according to the present invention in the fixating position.
Figure 5:
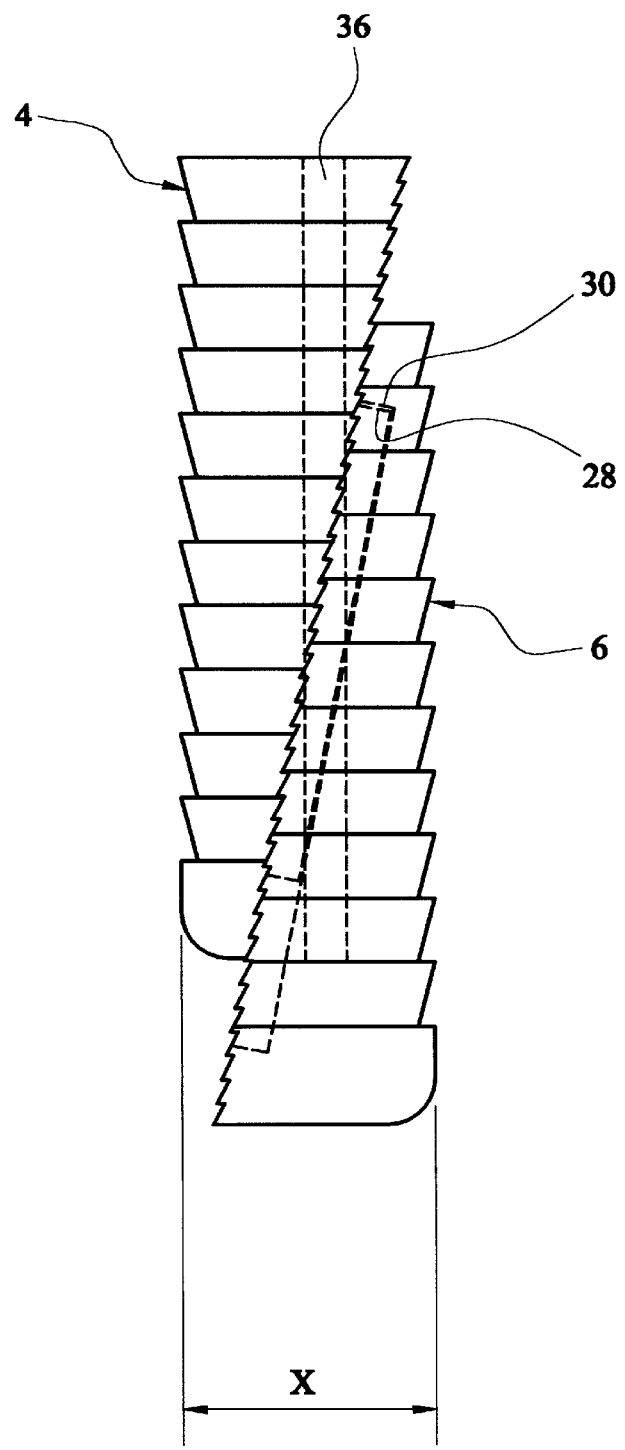
FIG. 5 shows a side elevation of the anchoring device in accordance with the present invention in the inserting position.

Referring to FIGS. 1–5, an anchoring device 2 comprises a first component 4 and a second component 6. In use, as best shown in FIG. 4, the anchoring device has a substantially tubular body with a series of equally spaced frusto-conical ridges formed on its outer surface to provide gripping engagement with the walls of the bone hole in use. The anchoring device is divided along its length into two wedge shaped components 4, 6. The first component 4 has an inner surface 8 extending from a trailing end 10 to a leading end 12 and has a series of interlockable ridges 14 projecting outwardly from the inner surface 8 thereof. Similarly, the second wedge shaped component 6 also has an inner surface 16 extending from a trailing end 18 to a leading end 20 thereof with a series of co-operating projections 22 extending from the inner surface 16 thereof. The projections 22 on the second component 6 are disposed at an opposite angle to the projections 14 on the first component 4. When the first and second component are mated together in the elongate arrangement shown in FIG. 5, the angle of the mating projections is such that it only allows movement in the direction which brings the component ends (12, 20, 18, 10) into contiguity and is progressively interlocked with respect to movement in the opposite direction. In the elongate position shown in FIG. 5, the anchoring device has an overall width x. Thereafter, the component 4 inner surface may be advanced along the inner surface of the second component 6 so that the anchoring device eventually increases in width to the dimension x+y depicted in FIG. 4 to thereby urge a transplant against the walls of a bone hole and fix the anchoring device in position.

Referring again to FIG. 1, the first component includes an integral elongate tongue 24 extending partially along the length thereof and projecting outwardly from its inner surface 8 and perpendicular thereto. In like manner, the inner surface 16 of the second component 6 includes an accommodating elongate groove 26 extending partially along the length thereof in such a manner that it extends to an equivalent amount as the tongue on component 4 in the direction of leading ends 12, 20 but extends to a greater extent than the tongue on component 4 in the direction of trailing ends 10, 18. Due to the greater extension of the groove in the direction of trailing ends 10, 18, the tongue may be located in the groove in the elongate position depicted in FIG. 5 so that the tongue trailing end 28 abuts against the groove trailing end 30 whereas in the maximum width position, depicted in FIG. 4, the tongue leading end 32 abuts against the groove leading end 34 preventing further advancement of the leading end 12 of the component 4 beyond the leading end 20 of the second component 6. Such an arrangement prevents any damage to transplant tissue located over the leading ends 12, 20 of the anchoring device.

Referring again to FIG. 5, the first component 4 has a positioning tool hole 36 extending therethrough spaced from and substantially parallel with the plane of the outer surface 38 of the first component 4. The hole is co-axial with the axis of the anchoring device in the said first component so that it exits partially along the surface of the tongue 24. A corresponding positioning tool hole is located in the second component 6 and forms a blind bore therein extending from a point partially along the groove 26 and parallel with the plane of the outer surface 44 of the component 6 and the axis of the anchor device. The positioning tool hole 42 formed in the second component 6 is slightly offset from the central axis of the anchoring device in the direction away from the first component to such an extent that it aligns with the positioning hole 36 in the first component 4 when they are positioned in the elongate position. Advantageously, this allows a positioning tool (not shown) to be inserted along the length of the positioning holes 36, 42 when the anchoring device is in the elongate position so that the anchoring device is interlocked by the positioning tool during insertion into the bone hole. After satisfactory insertion has taken place, the positioning tool may be removed or, at least partially removed so that it becomes free of the second component 6 and the first component 4 may then be advanced toward the end of the bone hole to thereby urge the ligament into the walls of the bone hole.

Figure 6:
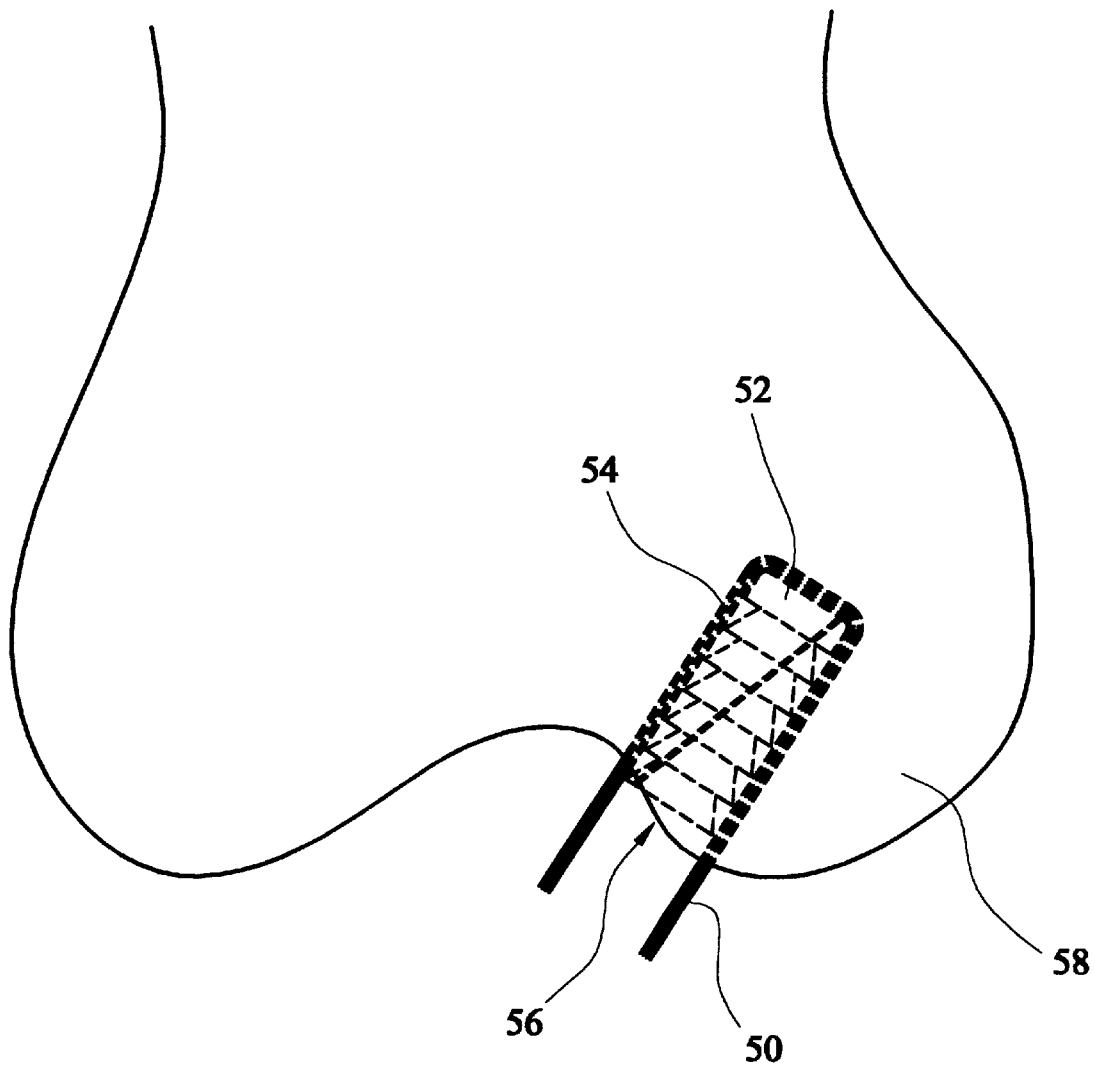
FIG. 6 shows an anchoring device in accordance with the present invention located in a bone hole in a femur.

Referring to FIG. 6, a replacement ligament 50 is shown looped over the end of an anchor device 52 in accordance with that previously described with respect to FIGS. 1–5. The anchoring device 52 urges the ligament 50 against the wall 54 of a bone hole 56 formed in a femoral bone 58. The formation of the bone hole 56 in the femur 58 is a standard surgical technique when reconstructing or replacing a torn or dislocated ligament, particularly, the anterior cruciate ligament (ACL) of the knee. A similar insertion can be made in the tibia (not shown).

The anchor device 52 is made from a suitably biocompatible material, preferably, a biodegradable material capable of being absorbed by the body. The leading end 53 of the anchor device was first located in and urged against the inner end of the bone hole before the trailing end 55 was advanced into a position contiguous therewith to provide a close fit in the bone hole and to urge the ligament against the walls of the bone hole.

An alternative use of the anchor is to anchor soft tissue by use of sutures. For example, the anchor may be used as a suture anchor for a rotator cut in the shoulder. In such cases, a suture anchor usually includes a transverse hole, formed in the anchor to anchor the sutures in position.

Figure 7:
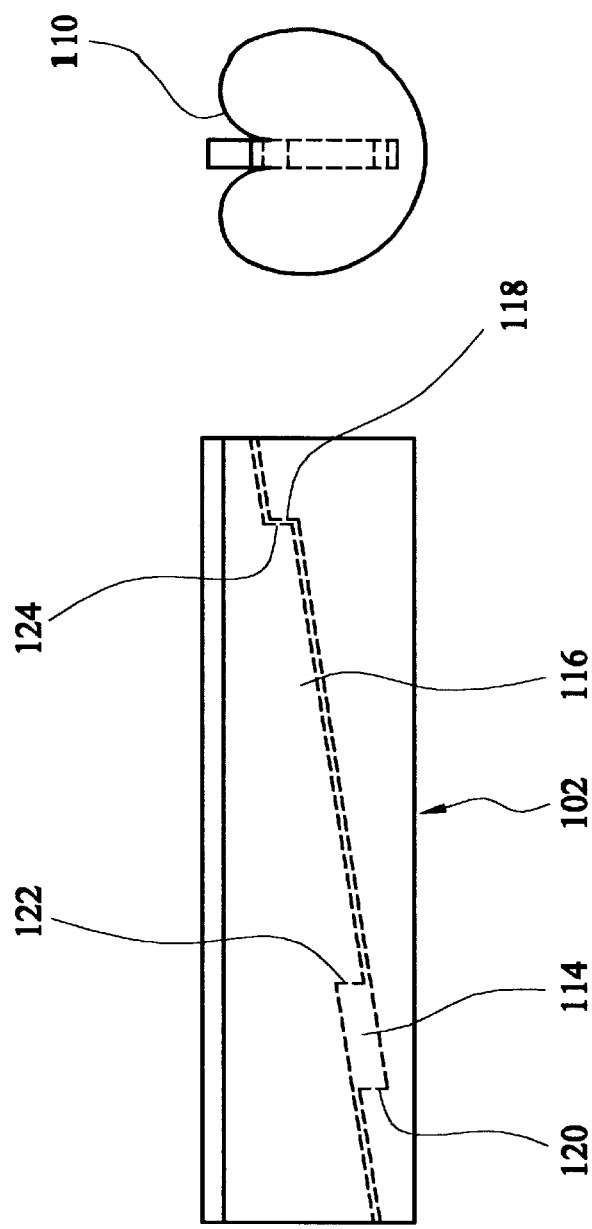
FIG. 7 shows an alternative embodiment of an anchoring device in accordance with the present invention.

Referring to FIG. 7, an alternative embodiment of the anchoring device of the invention is depicted. The anchor device 102 again comprises a first component 104 and a second component 106. The first component 104 has an outer surface designed to be received in a bone hole being substantially circular in cross section and being indented on one side by having an elongate recess 110 which has a co-extensive "U"-shaped channel 112 formed centrally therein. The blade 106 is designed for close fitting engagement with the "U"-shaped channel. The blade 106 is wedge shaped and has an integral co-planar tongue 116 depending therefrom which is slideably received in a corresponding groove section 114 integral with the main channel 112 and formed in the base thereof. The tongue is slideable in the channel 114 in the manner previously described with respect to FIGS. 1–5 between a leading end abutment 118 and a trailing end abutment 120 so that the overall width of the anchor device is adaptable between a narrower configuration wherein the trailing end 122 of the tongue 116 abuts the trailing end 120 of the groove 114 and a wider configuration wherein the leading end 124 of the tongue 116 abuts the leading abutment 118 of the groove 114. Conveniently, the elongate recess 110 formed at the top of the groove 112 provides, in use, together with the sides of the blade 106 a suitable channel to accommodate the transplant material on either side of the blade 106.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed in this specification (including any accompanying claims, abstract and drawings), or to any novel one, or any novel combination, of the steps of any method or process so disclosed.

What is claimed is:

1. An anchoring device for urging a ligament against a bone surface within a tunnel formed in a bone of a patient comprising a first component and a second component, the first and second component being designed for mutual sliding co-operation between a first anchor inserting position and a second fixation position, said sliding co-operation being provided along respective parallel inner mating surfaces of each component which surfaces are each in angular relation to the respective component outer surfaces and in opposed angular relation to each other so that in the anchor insertion position the width of the said anchoring device is in an elongate narrow mode with respect to a bone hole and, in the fixation position, the width of said anchoring device is in a compressed wide mode to thereby urge the ligament against a wall of the bone hole wherein the first or second component has an elongate tongue and the second or first component respectively has an accommodating elongate groove wherein the tongue slides in the groove between the said anchor inserting and fixating positions and wherein the groove comprises a terminal abutment at a leading end, said terminal abutment being the end adjacent to the inner end of the bone hole, in use, to provide a limit of longitudinal compression of the trailing component of the anchor device.

2. An anchoring device according to claim 1, wherein the first and second component include mutual engaging means on their respective inner surfaces for multiple position fixation.

3. An anchoring device according to claim 2, wherein the mutual engaging means provide incremental means to increasingly widen the anchor in the bone hole until a secure width is obtained.

4. An anchoring device according to claim 2, wherein the mutual engaging means is provided between mating surfaces.

5. An anchoring device according to claim 4, wherein the mutual engaging means is provided along inner surfaces adjacent to a tongue and/or groove and extending outwards substanially perpendicular thereto.

6. An anchoring device according to claim 1, wherein the groove also includes a terminal abutment at a trailing end, said terminal abutment being remote from the inner end of the bone hole to thereby provide a limit of extension of the anchor device.

7. An anchoring device according to claim 1, wherein the leading ends of the first and second components and a location of the leading end terminal abutment are such that the respective leading ends are substantially contiguous at a limit of compression to prevent damage to ligament located thereover.

8. An anchoring device according to claim 1, wherein trailing ends of the said first and second components are also substantially contiguous at a limit of said compression.

9. An anchoring device according to claim 1, wherein respective leading ends and respective trailing ends of the said first and second components are axially displaced from each other in an elongate inserting position of the anchor device.

10. An anchoring device according to claim 1, wherein an elongate positioning bore is provided in the anchor device.

11. An anchoring device according to claim 10, wherein said bore extends in two sections through both the first and second component in such a manner that the bore sections are aligned in a said first elongate position.

12. An anchoring device according to claim 11, wherein a positioning tool can be inserted through both bore sections in the said first anchor inserting position to thereby lock the two mating inner surfaces together during insertion in the bone hole.

13. An anchoring device according to claim 1, comprising grooves on the outer surface of the first and/or second component to conveniently locate and guide a ligament transplant thereon.

14. An anchoring device according to claim 1, wherein at least one groove is designed to accommodate a transplant on one side of the device.

15. An anchoring device according to claim 1 wherein said anchoring device in said compressed wide mode has a substantially tubular body with a series of ridges that circumscribe said tubular body and grip said wall of said bone hole.

16. An anchoring device according to claim 1, comprising outer surface means to accommodate said ligament on the outer surface of the first and/or second component.

17. An anchoring device according to claim 16, wherein said outer surface means is an ancillary groove.

18. An anchoring device comprising a first component and a second component, the first and second component being designed for mutual sliding co-operation between a first anchor inserting position and a second fixation position, said sliding co-operation being provided along respective parallel inner mating surfaces of each component which surfaces are each in angular relation to the respective component outer surfaces and in opposed angular relation to each other so that in the anchor insertion position the width of the said anchoring device is in an elongate narrow mode with respect to a bone hole and, in the fixation position, the width of said anchoring device is in a compressed wide mode to thereby urge the ligament against a wall of the bone hole, wherein the first component is shaped in the form of a blade, an outer edge of said blade (ie. the edge adjacent the walls of the bone hole in use) projecting out from the second component.

19. An anchoring device according to claim 18, wherein the inner edge of the blade provides a tongue for sliding in a groove of the second component.

20. An anchoring device according to claim 19, wherein leading and/or trailing ends of the blade are suitably stepped with respect to the respective leading and/or trailing ends of the tongue section to co-operate with respective terminal abutments in the groove and still provide contiguity with the second component in the fixation position.

21. A method of ligament fixation in a bone hole comprising the steps of:

forming a tunnel in a bone;

inserting a ligament transplant and an anchor device in the bone hole, said anchor device comprising a leading component and a trailing component, said leading component and trailing component adapted to slideably cooperate between a narrow first anchor insertion position and a second widened fixation position; and urging the trailing component into the fixating position to thereby urge the transplant against the bone hole and to fix the anchor in the said bone hole wherein said anchor device is adapted such that said leading component and said trailing component contact said ligament to fix the ligament in said bone hole.

22. A method of ligament fixation in a bone hole according to claim 21, wherein the method includes the step of:

inserting a positioning tool into the anchor device in said first anchor insertion position prior to locating the anchor device in the bone hole and utilising the positioning tool to locate the anchor device in the bone hole.

23. A method of ligament fixation in a bone hole according to claim 22, wherein the positioning tool is removed prior to urging the anchor device into the fixating position.

24. A method of ligament fixation in a bone hole according to claim 22, wherein after insertion is complete, the positioning tool is removed so that a trailing component may be pushed into the fixation position.

25. A method of ligament fixation in a bone hole according to claim 24, wherein pushing the trailing component into position progressively widens the anchor device to thereby urge the transplant against the walls of the bone hole and secure the anchor in position.

26. A method of ligament fixation in a bone hole according to claim 21, wherein a leading component is located in the fixation position whilst a trailing component remains in a trailing position during insertion.

27. A method of ligament fixation in a bone hole according to claim 21, wherein insertion of a trailing end progressively widens the anchor in the bone hole until a secure width is obtained.

28. A method of ligament fixation in a bone hole according to claim 27, wherein the secure width is that width wherein leading ends of the first and second component become contiguous.

* * * * *